United States Patent [19]

Skötsch et al.

[11] Patent Number: 4,517,367

[45] Date of Patent: May 14, 1985

[54] AZOLYL-PENTENE DERIVATIVES AND BIOCIDAL COMPOSITIONS CONTAINING THE SAME

[75] Inventors: Carlo Skötsch; Dietrich Baumert; Hansjörg Krähmer; Friedrich Arndt, all of Berlin, Fed. Rep. of Germany

[73] Assignee: Schering Aktiengesellschaft, Berlin and Bergkaman, Fed. Rep. of Germany

[21] Appl. No.: 447,624

[22] Filed: Dec. 6, 1982

[30] Foreign Application Priority Data

Dec. 4, 1981 [DE]  Fed. Rep. of Germany ....... 3148742

[51] Int. Cl.$^3$ ............... A01N 43/50; A01N 43/64; C07D 233/60; C07D 249/08
[52] U.S. Cl. .......................................... 546/276; 71/76; 71/90; 71/92; 71/69; 71/78; 546/278; 548/336; 548/341; 548/262
[58] Field of Search .............. 548/262, 336, 341; 542/453, 458, 466; 424/232, 269, 273 R, 263; 71/76, 92; 546/276, 278

[56] References Cited

U.S. PATENT DOCUMENTS 4,368,066  1/1983  Rentzea et al. ................ 71/92

Primary Examiner—Alton D. Rollins
Attorney, Agent, or Firm—Michael J. Striker

[57] ABSTRACT

Azolyl-pentene derivatives of the general formula $$CH_3-\underset{\underset{CH_3}{|}}{\overset{\overset{OR}{|}}{C}}-Z-\underset{\underset{R_1}{|}}{C}=C\overset{R_2}{\underset{H}{\diagdown}} \qquad I$$

in which
R is $C_1$–$C_{10}$-alkyl or $C_3$–$C_8$-alkenyl,
$R_1$ is imidazol-1-yl or 1,2,4-triazol-1-yl,
$R_2$ is aromatic hydrocarbon, aromatic hydrocarbon substituted one or more times, the same or differently, by halogen, $C_1$–$C_4$-alkoxy, $C_1$–$C_4$-alkyl, $C_1$–$C_4$-alkylthio, trifluoromethyl or nitro, or a heterocyclic hydrocarbon, and
Z is $$-\overset{\overset{O}{\|}}{C}- \quad \text{or} \quad -\overset{\overset{OH}{|}}{C}H-$$

and their acid addition salts with inorganic and organic acids. Also disclosed are processes for the production of these compounds as well as biocidal compositions containing the same.

77 Claims, No Drawings

AZOLYL-PENTENE DERIVATIVES AND BIOCIDAL COMPOSITIONS CONTAINING THE SAME

BACKGROUND OF THE INVENTION

The invention concerns new azolyl-pentene derivatives, processes for the production of theses compounds as well as biocidal compositions containing them, particularly with growth-regulatory effectiveness.

Geometrical isomers of triazol compounds and fungicides, herbicides and/or plant growth controlling agents containing these are already known (DE-OS No. 30 10 560). These compounds can indeed also be referred to for control of the growth of valuable plants, though it has been demonstrated that their effectiveness mainly with legumes and cotton is not sufficient.

SUMMARY OF THE INVENTION

It is therefore an object of the present invention to provide new azolyl-pentene derivatives, which are extensively usable and display a strong growth regulatory effectiveness particularly with legumes and cotton.

This object is attained according to the present invention by new azolyl-pentene derivatives of the general formula

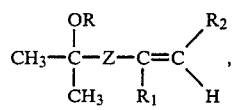

in which

R is $C_1-C_{10}$-alkyl or $C_3-C_8$-alkenyl.

$R_1$ is imidazol-1-yl or 1,2,4-triazol-1-yl, $R_2$ is an aromatic hydrocarbon, an aromatic hydrocarbon substituted one or more times the same or differently by halogen, $C_1-C_4$-alkoxy, $C_1-C_4$-alkyl, $C_1-C_4$-alkylthio, trifluoromethyl or nitro, or a heterocyclic hydrocarbon and Z is

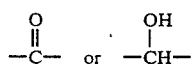

and their acid addition salts with inorganic and organic acids.

The compounds according to the present invention are biocidally effective in the broadest sense, distinguishing however particularly by a growth regulatory effectiveness, wherein they in surprising manner surpass known active substances of analogous constitution and utility.

Since the compounds according to the present invention bring about qualitative and quantitative alterations of the plants, they are classified in the category of plant growth regulators, which distinguish by the following possibilities of use:

Restraint of the vegetative growth of woody and herbal plants, for example at road borders, track systems, among others, in order to prevent too abundant a growth; growth restraint of grain, in order to prevent deposits or snapping off, and with cotton for increased yield.

Influencing the branching of vegetative and generative organs of ornamental and culture plants to increase the blossoming pieces or with tobacco and tomato to restrain side shoots.

Improving the fruit quality, for example an increase in sugar content for sugar cane, for sugar beets or for fruit, and a uniform maturity of the harvested goods, which leads to higher yields.

Increasing the resistance against climatic influences such as cold and dryness.

Influencing the latex flow of rubber plants.

Formation of parthenocarpic fruit, pollen sterility and sexual influences are likewise possibilities of use.

Control of the germination of seeds or the expulsion of buds.

Defoliating or influencing the fruit fall to facilitate harvesting.

The substances according to the present invention display their effectiveness not only with pre- but also with post-germination treatment. Their effectiveness is systematic.

They are suitable in particular for influencing the vegetative and generative growth of legumes, such as for example soy.

The amounts to be used, indeed depending upon purpose of use, are generally from 0.005 up to 5 kg active substance per hectare, but if necessary also greater application amounts can be used.

The time of use depends upon the purpose of use and the climatic conditions. Indeed according to type of plants and amount used, they can also provide certain herbicidal effects.

The compounds according to the present invention are suitable in surprising manner also for increasing the stress resistance of culture plants such as cotton, bushbean, cucumber, corn, soy and others.

Particularly to be emphasized is an increase of the resistance to drying.

This effect is of significance in so far as in considerable cultivated regions, many cultures must be artificially watered at great expenditure of energy. It has been estimated that in the year 2000 about two hundred million hectares of land will be watered.

A conditioning of the plants with the purpose that they would then only have to be provided with less water, or that they would be able to endure several days of dry periods without watering, would signify a great savings in both work and materials, and losses would drop.

In other respects also tillage surfaces can be cultivated which previously, based upon too great a dryness, could not be cultivated.

The fungicidal effectiveness applies in surprising manner against fungi of the most different systematic classification. With the treatment of above-ground plant parts, they protect against windborne pathogenic agents. Against seed-transportable pathogenic agents, the compounds can be used for the treatment of seeds. Moreover, they work systematically, that is, they are withdrawn from the roots of the plants, for example after being brought in with the sowing, are transported into the above-ground parts of the plants, and protect these against pathogenic agents.

The compounds according to the present invention display moreover a bactericidal effectiveness.

On account of the known broad activity spectrum the compounds are suitable not only for the protection of culture plants but also for material protection and for the control of human pathogenic and animal pathogenic microbes, whereby broadly multiplied use possibilities arise.

Indeed according to the specific meaning of the substituents, there are provided herewith key areas of use, with which the compounds display outstanding activities. They can thus always be used as plant growth regulators, fungicides or bactericides.

In the compounds designated by the general Formula I, the substituents can for example have the following meanings:

$R_1$ is $C_1$–$C_{10}$-alkyl, for example methyl, methyl, propyl, butyl, pentyl, hexyl, heptyl, octyl, nonyl, decyl, isopropyl, 2,2-dimethylpropyl-1, 3,3-dimethyl-butyl-2, $C_3$–$C_8$-alkenyl, for example allyl, 2-buten-1-yl, 3-methyl-2-buten-1-yl, hexenyl, heptenyl, octenyl;

$R_1$ is imidazol-1-yl or 1,2,4-triazol-1-yl;

$R_2$ is phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2,3-dichlorophenyl, 2,4-dichlorophenyl, 3,4-dichlorophenyl, 2,6-dichlorophenyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-butylphenyl, 3-butylphenyl, 4-butylphenyl, 2-sec.-butylphenyl, 3-sec.-butylphenyl, 2-tert.-butylphenyl, 3-tert.-butylphenyl, 2-methoxyphenyl, 4-methoxyphenyl, 2-ethoxyphenyl, 3-ethoxyphenyl, 4-ethoxyphenyl, 2-methylthiophenyl, 2-ethylthiophenyl, 3-ethylthiophenyl, 4-ethylthiophenyl, 2-trifluoromethylphenyl, 3-trifluoromethylphenyl, 4-trifluoromethylphenyl, 2-nitrophenyl, 3-nitrophenyl, 4-nitrophenyl, 3-fluoro-4-methoxyphenyl, 2-chloro-5-nitrophenyl, 4-chloro-2-fluorophenyl, 3,4,5-trimethoxyphenyl, 5-chloro-2-nitrophenyl, naphthyl, pyridyl, thienyl, furyl; and Z is —CO— or —CH(OH)—.

For formation of the acid addition salts, not only inorganic but also organic acids come into question. As examples, mention may be made of the following: hydrogen halogen acids, such as for example hydrochloric acid and hydrobromic acid, moreover phosphoric acid, sulfuric acid, nitric acid, mono- and bifunctional carboxylic acids and hydroxycarboxylic acids, such as for example acetic acid, maleic acid, oxalic acid, succinic acid, fumaric acid, tartaric acid, citric acid, salicylic acid, lactic acid, as well as sulfonic acids, such as for example p-toluenesulfonic acid and 1,5-naphthalinedisulfonic acid.

These acid addition salts can be obtained by customary salt formation processes, for example by dissolving a compound of the Formula I in a suitable solvent and addition of the acid.

An outstanding growth-regulatory effectiveness has been shown particularly for the following compounds:
1-(2,4-dichlorophenyl)-4-methoxy-4-methyl-2-(1,2,4-triazol-1-yl)-1-pentene-3-one
1-(2,6-dichlorophenyl)-4-methoxy-4-methyl-2-(1,2,4-triazol-1-yl)-1-pentene-3-one
4-methoxy-4-methyl-1-phenyl-2-(1,2,4-triazol-1-yl)-1-pentene-3-one
1-(4-chlorophenyl)-4-methoxy-4-methyl-2-(1,2,4-triazol-1-yl)-1-pentene-3-ol
1-(2,4-dichlorophenyl)-2-(imidazol-1-yl)-4-methoxy-4-methyl-1-pentene-3-one
1-(4-chlorophenyl)-4-methoxy-4-methyl-2-(1,2,4-triazol-1-yl)-1-pentene-3-one.

The following compounds according to the present invention provide an outstanding fungicidal effectiveness:
1-(4-chlorophenyl)-4-methoxy-4-methyl-2-(1,2,4-triazol-1-yl)-1-pentene-3-one
1-(2-chlorophenyl)-4-methoxy-4-methyl-2-(1,2,4-triazol-1-yl)-1-pentene-3-one
1-(4-chlorophenyl)-4-methoxy-4-methyl-2-(1,2,4-triazol-1-yl)-1-pentene-3-ol
1-(2,4-dichlorophenyl)-2-(imidazol-1-yl)-4-methoxy-4-methyl-1-pentene-3-one
4-methoxy-4-methyl-1-phenyl-2-(1,2,4-triazol-1-yl)-1-pentene-3-one.

As already mentioned, the compounds according to the present invention are transported systematically into the plant.

Correspondingly, they display not only upon application over the earth but also upon a spray treatment, their growth-regulatory effectiveness.

Particularly striking are growth restraining effects with legumes and cotton.

Aside from the previously described activities, the compounds according to the present invention also provide a bactericidal and herbicidal effectiveness, which permits further possibilities of use.

The compounds according to the present invention can be used either alone, in mixture with one another or with other active substances. If necessary, other plant protection or pest control agents can be added, indeed according to the desired purpose.

Expediently, the designated active substances or their mixtures are used in the form of preparations such as powders, sprays, granulates, solutions, emulsions or suspensions, with the addition of liquid and/or solid carrier substances or diluting agents and, if necessary, wetting, adhering, emulsifying and/or dispersing adjuvants.

Suitable liquid carriers include for example water, aliphatic and aromatic hydrocarbons, such as benzene, toluene, xylene, cyclohexanone, isopherone, dimethylsulfoxide, dimethylformamide, and moreover mineral oil fractions and plant oils.

Suitable as solid carriers are for example mineral earths such as tonsil, silica gel, talc, kaolin, attapulgite, limestone, silicic acid, and plant products, for example meal.

Surface-active substances worthy of mention include, for example, calcium lignin sulfonate, polyoxyethylenealkylphenyl-ether, naphthalinesulfonic acids and their salts, phenolsulfonic acids and their salts, formaldehyde condensate, fatty alcohol sulfate as well as substituted benzene sulfonic acids and their salts.

To the extent that the active substances should find use for seed disinfection, also dyes can be admixed, in order to provide the drenched seeds with a clearly visible coloration.

The portion of active substance(s) in the various preparations can vary within broad limits. For example, the composition can contain about 10–90% by weight active substance, about 90–10% by weight liquid or solid carrier, as well as if necessary up to 20% by weight surface-active substances, upon corresponding reduction of the amount of active substance or carrier.

The application of the composition can follow in customary manner, for example with water as carrier in spray broth amounts from about 100 up to about 1000 liter/ha. A use of the composition in the so-called "low-volume" or "ultra-low-volume" techniques is likewise possible, as is their application in the form of so-called microgranulates.

For production of the preparations, the following components may be used, for example:

A. Spray Powder (a)
40% by weight active substance
25% by weight clay minerals
20% by weight silicic acid
10% by weight cell pitch
5% by weight surface-active substance based upon a mixture of the calcium salt of lignin sulfonic acid with alkylphenolpolyglycolethers (b)
25% by weight active substance
60% by weight kaolin
10% by weight silicic acid
5% by weight surface-active substance based upon the sodium salt of N-methyl-N-oleyl-taurine and the calcium salt of lignin sulfonic acid.

(c)
10% by weight active substance
60% by weight clay minerals
15% by weight silicic acid
10% by weight cell pitch
5% by weight surface-active substance on the basis of the sodium salt of N-methyl-N-oleyl-taurine and the calcium salt of lignin sulfonic acid.

B. Paste
45% by weight active substance
5% by weight sodium aluminum silicate
15% by weight cetylpolyglycolether with 8 mol ethylene oxide
2% by weight spindle oil
10% by weight polyethyleneglycol
23 parts water C. Emulsion Concentrate
25% by weight active substance
15% by weight cyclohexanone
55% by weight xylene
5% by weight mixture of nonylphenylpolyoxyethylene or calcium dodecylbenzenesulfonate.

The new compounds according to the present invention can be produced for example by condensing compounds of the general formula

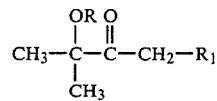   II with compounds of the general Formula

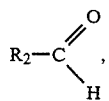   III if necessary dissolved in a solvent and in the presence of a catalyst, and the reaction product of general Formula I with Z having the meaning —CO— can if desired be reduced to the corresponding compounds with Z having the meaning —CH(OH)—, wherein R, $R_1$ and $R_2$ have the above given meaning.

The condensation is performed according to known methods. In general, one reacts therewith 1 mol of 3-alkoxy-1-(azol-1-yl)-3-methyl-2-butanone of the general Formula II with one to two mole of the aldehyde of the general Formula III, if necessary using a suitable solvent and in the presence of a catalyst. Catalysts can for example be: alkali or earth-alkali metal hydroxides, such as sodium, potassium or calcium hydroxide, alkali metal alcoholates, such as sodium methylate, sodium ethylate or potassium methylate, carbonates, for example sodium or potassium carbonate, acetates, for example sodium or potassium acetate, secondary amines, for example diethylamine, dipropylamine, pyrrolidine, piperidine or morpholine, and tertiary amines, such as triethylamine, tributylamine, pyridine, picoline or dimethylaniline. The catalyst is provided in an amount from 0.5 up to 0.0 mol. Useful solvents include for example alcohols, such as methanol or ethanol, aromatic hydrocarbons, such as benzene, toluene or xylene, ethers, such as diethylether, tetrahydrofuran or dioxane, water and mixtures thereof. The reaction follows in expedient manner in the range from 0° C. up to the boiling point of the particular solvent.

When as catalyst an acetate, for example sodium or potassium acetate, a carbonate, for example sodium or potassium carbonate, or a tertiary amine is used, then glacial acetic acid or acetic acid anhydride can be used as reaction solvent.

Purification of the compounds follows generally by recrystallization or column chromatography.

In order to provide compounds of the general Formula I with Z exclusively having the meaning —CH(OH)—, i.e., the 4-alkoxy-1-aryl-2-(azol-1-yl)-4-methyl-1-pentene-3-ols, one proceeds by reduction of the corresponding on-compounds of the general Formula I with Z=—CO—. For this purpose one uses in a suitable solvent a metal complex, for example lithium aluminum hydride or sodium borohydride or an aluminum alkoxide, for example aluminum isopropylate. As solvent for the reduction with lithium aluminum hydride, for example ethers such as diethylether or tetrahydrofuran are suitable. The reaction temperature lies preferably between −20° and +60° C. Upon use of sodium borohydride, particularly ethers, such as diethylether or tetrahydrofuran, alcohols such as methanol, ethanol or isopropanol are suitable as solvent. The reaction temperature amounts preferably to between 0° C. and room temperature. When as reducing agent aluminum isopropylate is used, as solvent preferably alcohol such as isopropanol or aromatic hydrocarbon such as toluene should be used.

The purification of the compound follows generally through recrystallization or through column chromatography.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

1-(4-chlorophenyl)-4-methoxy-4-methyl-2-(1,2,4-triazol-1-yl)-1-pentene-3-one 26.8 g (0.146 mol) 3-methoxy-3-methyl-1-(1,2,4-triazol-1-yl)-2-butanone are provided with 21.38 g (0.152 mol) 4-chlorobenzaldehyde in 85 ml acetic acid anhydride. After heating to 50° C., 20 ml triethylamine are added dropwise. The reaction mixture is then stirred for 4.5 hours at 70° C., allowed to stand overnight, and then compressed to dryness in a vacuum rotation evaporator.

It is then taken up in 500 ml acetic acid ethylester, washed twice, each time with 300 ml diluted potassium hydrogen carbonate solution and subsequently twice, each time with 200 ml water. The organic phase is dried across magnesium sulfate and, after filtration, compressed in a vacuum rotation evaporator. The remaining dark brown oil is crystallized after the addition of hexane. It is then recrystallized from diisopropylether.

Yield: 21 g (47% of theoretical amount).
MP: 102°–104° C.

EXAMPLE 2

1-(2-chlorophenyl)-4-methoxy-4-methyl-2-(1,2,4-triazol-1-yl)-1-pentene-3-ol 10 g (0.0327 mol) 1-(2-chlorophenyl)-4-methoxy-4-methyl-2-(1,2,4-triazol-1-yl)-pentene-3-one are provided in 25 ml methanol. At 0°–10° C., under stirring and over a 15 minute period, 0.57 g (0.015 mol) sodium borohydride are introduced. The mixture is stirred for one hour, rotated in a vacuum, reacted with acetic acid and the solution is subsequently made alkaline with $K_2CO_3$ solution. It is then extracted with acetic ester, the acetic ester phase is dried across magnesium sulfate, followed by filtration, rotation and recrystallization of the residue from diisopropylether.

Yield: 5.2 g = 51.7% of theoretical amount.
MP: 116°–118° C.

In analogous manner, the following compounds according to the present invention are produced:

| Name of the Compound | Physical Constant |
|---|---|
| 1-(2-chlorophenyl)-4-methoxy-4-methyl-2-(1,2,4-triazol-1-yl)-1-pentene-3-one | MP: 95–98° C. |
| 1-(2,4-dichlorophenyl)-4-methoxy-4-methyl-2-(1,2,4-triazol-1-yl)-1-pentene-3-one | MP: 89–91° C. |
| 1-(2,6-dichlorophenyl)-4-methoxy-4-methyl-2-(1,2,4-triazol-1-yl)-1-pentene-3-one | MP: 100–103° C. |
| 4-methoxy-4-methyl-1-phenyl-2-(1,2,4-triazol-1-yl)-1-pentene-3-one | MP: 76–80° C. |
| 1-(4-chlorophenyl)-2-(imidazol-1-yl)-4-methoxy-4-methyl-1-pentene-3-one | MP: 70–73° C. |
| 4-methoxy-4-methyl-1-(2-thienyl)-2-(1,2,4-triazol-1-yl)-1-pentene-3-one | MP: 94–97° C. |
| 2-(imidazol-1-yl)-4-methoxy-4-methyl-1-(2-thienyl)-1-pentene-3-one | MP: 72–76° C. |
| 1-(2,4-dichlorophenyl)-2-(imidazol-1-yl)-4-methoxy-4-methyl-1-pentene-3-one | MP: 105–108° C. |
| 1-(2,6-dichlorophenyl)-2-(imidazol-1-yl)-4-methoxy-4-methyl-1-pentene-3-one | MP: 97–99° C. |
| 1-(2-chlorophenyl)-2-(imidazol-1-yl)-4-methoxy-4-methyl-1-pentene-3-one | MP: 72–75° C. |
| 2-(imidazol-1-yl)-4-methoxy-4-methyl-1-phenyl-1-pentene-3-one | MP: 67–70° C. |
| 1-(2,4-dichlorophenyl)-4-methoxy-4-methyl-2-(1,2,4-triazol-1-yl)-1-pentene-3-ol | MP: 175–177° C. |
| 1-(3,4-dichlorophenyl)-4-methoxy-4-methyl-2-(1,2,4-triazol-1-yl)-1-pentene-3-one, naphthaline disulfonate | MP: 227–232° C. |
| 1-(2,6-dichlorophenyl)-4-methoxy-4-methyl-2-(1,2,4-triazol-1-yl)-1-pentene-3-ol | MP: 128–130° C. |
| 1-(4-chlorophenyl)-4-methoxy-4-methyl-2-(1,2,4-triazol-1-yl)-1-pentene-3-ol | MP: 126° C. |
| 4-methoxy-4-methyl-1-(2-thienyl)-2-(1,2,4-triazol-1-yl)-1-pentene-3-ol | MP: 131–136° C. |
| 1-(4-bromophenyl)-4-methoxy-4-methyl-2-(1,2,4-triazol-1-yl)-1-pentene-3-one | MP: 102–105° C. |
| 4-ethoxy-(4-chlorophenyl)-4-methyl-2-(1,2,4-triazol-1-yl)-1-pentene-3-one | MP: 105–107° C. |
| 4-ethoxy-(4-fluorophenyl)-4-methyl-2-(1,2,4-triazol-1-yl)-1-pentene-3-one | MP: 57–60° C. |
| 1-(4-fluorophenyl)-4-methoxy-4-methyl-2-(1,2,4-triazol-1-yl)-1-pentene-3-one | MP: 104–107° C. |
| 1-(3-chlorophenyl)-4-methoxy-4-methyl-2-(1,2,4-triazol-1-yl)-1-pentene-3-one | $n_D^{20}$: 1.5480 |
| 1-(4-bromophenyl)-4-methoxy-4-methyl-2-(1,2,4-triazol-1-yl)-1-pentene-3-ol | MP: 129–133° C. |
| 4-ethoxy-4-methyl-1-phenyl-(1,2,4-triazol-1-yl)-1-pentene-3-one | $n_D^{20}$: 1.5580 |
| 4-ethoxy-1-(2-chlorophenyl)-4-methyl-2-(1,2,4-triazol-1-yl)-1-pentene-3-one | $n_D^{20}$: 1.5610 |
| 4-ethoxy-4-methyl-1-(4-nitrophenyl)-2-(1,2,4-triazol-1-yl)-1-pentene-3-one | $n_D^{20}$: 1.5660 |
| 4-ethoxy-(3-chlorophenyl)-4-methyl-2-(1,2,4-triazol-1-yl)-1-pentene-3-one | $n_D^{20}$: 1.5535 |
| 4-ethoxy-1-(4-chlorophenyl)-4-methyl-2-(1,2,4-triazol-1-yl)-1-pentene-3-ol | MP: 142–144° C. |
| 1-(4-fluorophenyl)-4-methoxy-4-methyl-2-(1,2,4-triazol-1-yl)-1-pentene-3-ol | MP: 90.5–93.5° C. |
| 4-ethoxy-1-(4-bromophenyl)-4-methyl-2-(1,2,4-triazol-1-yl)-1-pentene-3-one | MP: 110–112° C. |
| 4-ethoxy-1-(2,4-dichlorophenyl)-4-methyl-2-(1,2,4-triazol-1-yl)-1-pentene-3-one | $n_D^{20}$: 1.5700 |
| 4-ethoxy-1-(3,4-dichlorophenyl)-4-methyl-2-(1,2,4-triazol-1-yl)-1-pentene-3-one | MP: 83–85° C. |
| 4-ethoxy-4-methyl-1-(4-methylphenyl)-2-(1,2,4-triazol-1-yl)-1-pentene-3-one | MP: 84–87° C. |
| 4-ethoxy-4-methyl-1-phenyl-2-(1,2,4-triazol-1-yl)-1-pentene-3-ol | MP: 88–92° C. |
| 4-ethoxy-1-(4-fluorophenyl)-4-methyl-2-(1,2,4-triazol-1-yl)-1-pentene-3-ol | MP: 125–127° C. |
| 4-ethoxy-1-(2-chlorophenyl)-4-methyl-2-(1,2,4-triazol-1-yl)-1-pentene-3-ol | MP: 142–145° C. |
| 1-(2-fluorophenyl)-4-methoxy-4-methyl-2-(1,2,4-triazol-1-yl)-1-pentene-3-one | $n_D^{20}$: 1.5380 |
| 4-methoxy-1-(4-methoxyphenyl)-4-methyl-2-(1,2,4-triazol-1-yl)-1-pentene-3-one | $n_D^{20}$: 1.5870 |
| 4-ethoxy-4-methyl-1-(4-nitrophenyl)-2-(1,2,4-triazol-1-yl)-1-pentene-3-ol | MP: 180–182° C. |
| 4-ethoxy-1-(4-bromophenyl)-4-methyl-2-(1,2,4-triazol-1-yl)-1-pentene-3-ol | MP: 148–152° C. |
| 4-ethoxy-1-(2,4-dichlorophenyl)-4-methyl-2-(1,2,4-triazol-1-yl)-1-pentene-3-ol | MP: 148–152° C. |

| Name of the Compound | Physical Constant |
|---|---|
| 4-ethoxy-1-(3,4-dichlorophenyl)-4-methyl-2-(1,2,4-triazol-1-yl)-1-pentene-3-ol | MP: 115–117° C. |
| 4-ethoxy-4-methyl-1-(4-methylphenyl)-2-(1,2,4-triazol-1-yl)-1-pentene-3-ol | MP: 120–123° C. |
| 4-ethoxy-1-(4-methoxyphenyl)-4-methyl-2-(1,2,4-triazol-1-yl)-1-pentene-3-one | MP: 135–137° C. |
| 4-ethoxy-1-(2-furyl)-4-methyl-2-(1,2,4-triazol-1-yl)-1-pentene-3-one | $n_D^{20}$: 1.5650 |
| 4-ethoxy-1-(2-furyl)-4-methyl-2-(1,2,4-triazol-1-yl)-1-pentene-3-ol | MP: 124–127° C. |
| 4-ethoxy-1-(4-methoxyphenyl)-4-methyl-2-(1,2,4-triazol-1-yl)-1-pentene-3-one | MP: 112–115° C. |
| 4-ethoxy-4-methyl-1-(2-thienyl)-2-(1,2,4-triazol-1-yl)-1-pentene-3-ol | MP: 138–140° C. |
| 4-ethoxy-4-methyl-1-(2-methylphenyl)-2-(1,2,4-triazol-1-yl)-1-pentene-3-ol | MP: 148–152° C. |
| 4-ethoxy-4-methyl-1-(3-pyridyl)-2-(1,2,4-triazol-1-yl)-1-pentene-3-one | |
| 4-ethoxy-4-methyl-1-(3-pyridyl)-2-(1,2,4-triazol-1-yl)-1-pentene-3-ol | |
| 4-ethoxy-4-methyl-1-(2-naphthyl)-2-(1,2,4-triazol-1-yl)-1-pentene-3-one | MP: 85–89° C. |
| 4-ethoxy-4-methyl-1-(2-naphthyl)-2-(1,2,4-triazol-1-yl)-1-pentene-3-ol | MP: 152–154° C. |
| 4-methoxy-4-methyl-1-(4-methylphenyl)-2-(1,2,4-triazol-1-yl)-1-pentene-3-one | MP: 72–76° C. |
| 4-methoxy-4-methyl-1-(4-methylphenyl)-2-(1,2,4-triazol-1-yl)-1-pentene-3-ol | MP: 110–113° C. |
| 4-methoxy-1-(4-methoxyphenyl)-4-methyl-2-(1,2,4-triazol-1-yl)-1-pentene-3-ol | MP: 90.5–95.5° C. |
| 4-methoxy-4-methyl-1-phenyl-2-(1,2,4-triazol-1-yl)-1-pentene-3-ol | MP: 77–82° C. |
| 1-(3,4-dichlorophenyl)-4-methoxy-4-methyl-2-(1,2,4-triazol-1-yl)-1-pentene-3-one | MP: 80–82° C. |
| 1-(3,4-dichlorophenyl)-4-methoxy-4-methyl-2-(1,2,4-triazol-1-yl)-1-pentene-3-ol | MP: 115–119° C. |
| 4-methoxy-4-methyl-1-(4-nitrophenyl-2-(1,2,4-triazol-1-yl)-1-pentene-3-one | MP: 124–128° C. |
| 4-methoxy-4-methyl-1-(4-nitrophenyl)-2-(1,2,4-triazol-1-yl)-1-pentene-3-ol | MP: 157–160° C. |
| 4-methoxy-4-methyl-1-(2-methylphenyl)-2-(1,2,4-triazol-1-yl)-1-pentene-3-one | MP: 72–76° C. |
| 4-methoxy-4-methyl-1-(2-methylphenyl)-2-(1,2,4-triazol-1-yl)-1-pentene-3-ol | MP: 128–133° C. |
| 1-(2-chlorophenyl)-2-(imidazol-1-yl)-4-methoxy-4-methyl-1-pentene-3-ol | MP: 154–158° C. |
| 1-(4-chlorophenyl)-2-(imidazol-1-yl)-4-methoxy-4-methyl-1-pentene-3-ol | MP: 90–95° C. |
| 4-ethoxy-1-(3-chlorophenyl)-4-methyl-2-(1,2,4-triazol-1-yl)-1-pentene-3-ol | MP: 114–116° C. |
| 1-(3-chlorophenyl)-4-methoxy methyl-2-(1,2,4-triazol-1-yl)-1-pentene-3-ol | MP: 80–84° C. |
| 4-n-butoxy-1-(4-chlorophenyl)-4-methyl-2-(1,2,4-triazol-1-yl)-1-pentene-3-ol | MP: 85° C. |
| 4-n-butoxy-1-(2-chlorophenyl)-4-methyl-2-(1,2,4-triazol-1-yl)-1-pentene-3-ol | MP: 95° C. |
| 4-ethoxy-1-(2-fluorophenyl)-4-methyl-2-(1,2,4-triazol-1-yl)-1-pentene-3-one | $n_D^{20}$: 1.5370 |
| 4-(n-butoxy)-1-(4-chlorophenyl)-4-methyl-2-(1,2,4-triazol-1-yl)-1-pentene-3-one | $n_D^{20}$: 1.5430 |
| 4-(n-butoxy)-1-(2-chlorophenyl)-4-methyl-2-(1,2,4-triazol-1-yl)-1-pentene-3-one | $n_D^{20}$: 1.5490 |
| 4-methoxy-4-methyl-1-(2-pyridyl)-2-(1,2,4-triazol-1-yl)-1-pentene-3-ol | MP: 104° C. |

The compounds according to the present invention dissolve poorly in water and more or less well in polar organic solvents, such as alcohols, for example methanol, ethanol, among others, as well as acetic acid ethylester, diethylether, diisopropylether, acetonitrile and N,N-dimethylformamide.

They dissolve well in organic solvents, such as for example chloroform, methylene chloride, toluene and xylene.

The compounds according to the present invention can be present as Z,E-isomers, and as pure Z- or E-forms. Accordingly, it is to be understood that all isomers belong to the subject of the present invention.

The starting products for production of the compounds according to the present invention are known per se or can be prepared according to known methods.

EXAMPLE 3

Soy plants are grown in a greenhouse up to the stage of primary leaves. The compounds according to the present invention are sprayed as aqueous emulsions in application amounts of 0.1 and 0.5 kg active substance per hectare onto the plants. 3 weeks after the application, the total lengths of the plants are determined and the restraint in growth evaluated in comparison to the control.

| Compound according to the Invention | Growth Restraint in % | |
|---|---|---|
| | 0.1 kg active agent/ha | 0.5 kg active agent/ha |
| 1-(2,4-dichlorophenyl)-4-methoxy-4-methyl-2-(1,2,4-triazol-1-yl)-1-pentene-3-one | 13 | 17 |
| 1-(2,6-dichlorophenyl)-4-methoxy-4-methyl-2-(1,2,4-triazol-1-yl)-1-pentene-3-one | 11 | 21 |
| 4-methoxy-4-methyl-1-phenyl-2-(1,2,4-triazol-1-yl)-1-pentene-3-one | 3 | 17 |
| 1-(4-chlorophenyl)-4-methoxy-4-methyl-2-(1,2,4-triazol-1-yl)-1-pentene-3-ol | 53 | 75 |
| Comparison Agent | | |
| 2-chloroethyltrimethyl-ammonium chloride (chlormequatschloride) | 15 | 16 |
| 2-chloroethylphosphonic acid (Ethephon) | 0 | 11 |

EXAMPLE 4

Soy plants in a stage of pre-germination are treated with aqueous emulsions of the compounds to be tested, in application amounts of 0.5 and 1.0 kg active substance per hectare, and cultivated in a greenhouse.

After 3 weeks the total length of the plants and the percent growth restraint in comparison to the control is determined. Moreover, from the primary leaves, a leaf disk of 1.7 cm diameter is punched out. The chlorophyll is extracted from these disks. The amount of chlorophyll is determined photometrically at 665 nm, and the percent increase in comparison to the control is calculated.

From the following Table, it is evident that the intensive growth-regulatory effectiveness of the compounds according to the present invention clearly differs from that of the corresponding comparison compounds.

|  | 0.5 kg active agent/ha growth restraint, % | chlorophyll-content increase in % | 1.0 kg active agent/ha growth restraint, % | chlorophyll-content increase in % |
| --- | --- | --- | --- | --- |
| Compound according to the Invention |  |  |  |  |
| 1-(4-chlorophenyl)-4-methoxy-4-methyl-2-(1,2,4-triazol-1-yl)-1-pentene-3-one | 33 | 5.8 | 71 | 9.7 |
| 1-(2,4-dichlorophenyl)-2-(imidazol-1-yl)-4-methoxy-4-methyl-1-pentene-3-one | 10 | 15.5 | 11 | 17.5 |
| 1-(4-chlorophenyl)-4-methoxy-4-methyl-2-(1,2,4-triazol-1-yl)-1-pentene-3-one | 84 | 27.4 | 91 | 56.5 |
| Comparison Agent from DE-OS 30 10 560 |  |  |  |  |
| 1-(4-chlorophenyl)-4,4-dimethyl-2-(1,2,4-triazol-1-yl)-1-pentene-3-one | 6 | 1.4 | 19 | 0.8 |
| 1-(4-chlorophenyl)-4,4-dimethyl-2-(1,2,4-triazol-1-yl)-1-pentene-3-ol | 74 | 12.5 | 86 | 36.3 |

EXAMPLE 5

Cotton plants, in a stage of pre-germination, are treated with aqueous emulsions of the compounds to be tested, in application amounts of 1 kg active substance per hectare. After 3 weeks cultivation in a greenhouse, the total length of the plants is determined and the percent growth restraint is calculated.

From the following Table the effectiveness advantage of the compound according to the present invention is evident.

| Compound according to the Invention | Percent Growth Restraint |
| --- | --- |
| 1-(4-chlorophenyl)-4-methoxy-4-methyl-2-(1,2,4-triazol-1-yl)-1-pentene-3-ol | 54 |
| Comparison Agent |  |
| 2-chloroethylphosphonic acid (Ethephon) | 0 |
| 1,1-dimethyl-piperidinum-chloride (Mepiquat chloride) | 0 |

EXAMPLE 6

Barley, in the stage of pre-germination, is treated with aqueous emulsions of the compounds to be tested, in application amounts of 0.5 and 1 kg active substance per hectare. After 3 weeks cultivation in a greenhouse, the total length of the plants is determined and the percent growth restraint calculated.

The test results show clearly the growth restraint caused by the compound according to the present invention with Gramine, for example barley. The comparison agents demonstrate, in contrast thereto, no effectiveness.

|  | Percent Growth Restraint | |
| --- | --- | --- |
| Compound according to the Invention | 0.5 kg active agent/ha | 1.0 kg active agent/ha |
| 1-(4-chlorophenyl)-4-methoxy-4-methyl-2-(1,2,4-triazol-1-yl)-1-pentene-3-ol | 22 | 35 |
| Comparison Agents |  |  |
| 2-chloroethylphosphoric acid (Ethephon) | 0 | 0 |
| 2-chloroethyltrimethyl ammonium chloride (Chlormequat chloride) | 0 | 0 |

EXAMPLE 7

Bushbeans, in the stage of pre-germination, are treated with aqueous emulsions of the compounds to be tested, in application amounts of 0.5–1.0 and 2.0 kg active substance per hectare. After 3 weeks, the growth in length of the plants is measured and the percent growth restraint calculated.

From the primary leaves, moreover, leaf disks having a diameter of 1.7 cm are punched out. The chlorophyll is extracted from these leaf disks and the chlorophyll-a-content is determined photometrically at 665 nm. From the following Table may be seen the increase in the chlorophyll-a-content in percent. The clearly evident effectiveness advantage of the compound according to the present invention in comparison to the known compound comes to light.

| | Growth Restraint and Chlorophyll-Content Increase with Bush Bean | | | | | |
|---|---|---|---|---|---|---|
| | Growth Restraint in % (kg actv. subst./ha) | | | Chlorophyll-content increase in % (kg actv. subst./ha) | | |
| | 0.5 | 1.0 | 2.0 | 0.5 | 1.0 | 2.0 |
| Compound according to the Invention | | | | | | |
| 1-(4-chlorophenyl)-4-methoxy-4-methyl-2-(1,2,4-triazol-1-yl)-1-pentene-3-one | 17 | 60 | 67 | 40.7 | 57.4 | 85.3 |
| 1-(4-chlorophenyl)-4-methoxy-4-methyl-2-(1,2,4-triazol-1-yl)-1-pentene-3-ol | 92 | 93 | 93 | 154.4 | 203.9 | 210.3 |
| Comparison Agent (from DE-OS 30 10 560) | | | | | | |
| 1-(4-chlorophenyl)-4,4-dimethyl-2-(1,2,4-thiazol-1-yl)-1-pentene-3-ol | 75 | 83 | 93 | 121.6 | 130.9 | 158.3 |

EXAMPLE 8

Cotton, bush beans and soybeans, in the stage of pre-germination, are sprayed with aqueous emulsions of the compounds according to the present invention, in application amounts of 0.1, 0.3, 1 and 3 kg active substance/ha, placed in a greenhouse, and uniformly sprayed with water. After 3 weeks cultivation, the spraying is adjusted and classified in one or more days intervals. The following classification scheme is used:

0 = plants completely turgescent
1 = symptoms of decay
2 = leaves decayed
3 = leaves strongly decayed
4 = leaves dry, paper-like Classification is made 1, 2 and 5 days after adjusting the spraying.

| | Application Amount kg active agent/ha | peas | tomato |
|---|---|---|---|
| Compound according to the Invention | | | |
| 1-(4-chlorophenyl)-4-methoxy-4-methyl-2-(1,2,4-triazol-1-yl)-1-pentene-3-one | 1 | 53 | 12 |
| | 2 | 66 | 25 |
| 1-(4-chlorophenyl)-4-methoxy-4-methyl-2-(1,2,4-triazol-1-yl)-1-pentene-3-ol | 1 | 73 | 62 |
| | 2 | 73 | 75 |
| Comparison Agent | | | |
| 1-(4-chlorophenyl)-4,4-dimethyl-2-(1,2,4-triazol-1-yl)-1-pentene-3-ol | 1 | 53 | 62 |
| | 2 | 73 | 62 |

The results show that the compound according to the present invention, at an application amount of 1 kg

| | Application Amount kg active agent/ha | Cotton | | | Bush Bean | | | Soybean | | |
|---|---|---|---|---|---|---|---|---|---|---|
| | | 1 | 2 | 5 days | 1 | 2 | 5 days | 1 | 2 | 5 days |
| Compound according to the Invention | | | | | | | | | | |
| 1-(4-chlorophenyl)-4-methoxy-4-methyl-2-(1,2,4-triazol-1-yl)-1-pentene-3-one | 0.1 | — | — | — | — | — | — | ¾ | 4 | 4 |
| | 0.3 | — | — | — | — | — | — | 2 | 4 | 4 |
| | 1.0 | — | — | — | — | — | — | 1 | 2 | 4 |
| | 3.0 | — | — | — | — | — | — | 0 | 1 | 4 |
| 1-(4-chlorophenyl)-4-methoxy-4-methyl-2-(1,2,4-triazol-1-yl)-1-pentene-3-ol | 0.1 | 0 | 2 | 3 | 0 | 0 | 4 | 0 | 1 | 4 |
| | 0.3 | 0 | 1 | 3 | 0 | 0 | 3 | 0 | 0 | 3 |
| | 1.0 | 0 | 0 | 2 | 0 | 0 | 2 | 0 | 0 | 2 |
| | 3.0 | 0 | 0 | 2 | 0 | 0 | 2 | 0 | 0 | 2 |
| Control | | 1 | 3 | 4 | 2 | 4 | 4 | ¾ | 4 | 4 |

—: no test

The Table shows that the compounds according to the present invention endow the plants with a higher resistance to drying. Whereas with all controls, indeed after 1 or 2 days a strong decay occurs, treated plants can manage in part more than 2 days without spraying.

EXAMPLE 9

Peas and tomatoes, in the stage of pre-germination, are sprayed with aqueous emulsions of the compounds, in application amounts of 1 and 2 kg active substance per hectare. After 3 weeks greenhouse cultivation, plant length and percent growth restraint are determined. In the Table the results are set forth:

active substance per hectare produces the same effect as the comparison agent at an application amount of 2 kg active substance/hectare.

EXAMPLE 10

Soybeans, in a stage of pre-germination, are sprayed with aqueous emulsions of the compounds according to the present invention, in an application amount of 0.5 kg active substance per hectare, placed in a greenhouse, and uniformly sprayed with water. After three weeks cultivation, the spraying is adjusted. 4 days later classification is performed according to the scheme for Example 8:

| Compound according to the Invention | Classification |
|---|---|
| 4-methoxy-4-methyl-1-(2-thienyl)-2-(1,2,4-triazol-1-yl)-1-pentene-3-ol | 2 |
| 1-(4-bromophenyl)-4-methoxy-4-methyl-2-(1,2,4-triazol-1-yl)-1-pentene-3-one | 2 |
| 1-(3-chlorophenyl)-4-methoxy-4-methyl-2-(1,2,4-triazol-1-yl)-1-pentene-3-one | 1 |
| 1-(4-bromophenyl)-4-methoxy-4-methyl-2-(1,2,4-triazol-1-yl)-1-pentene-3-ol | 0 |
| 4-ethoxy-1-(4-chlorphenyl)-4-methyl-2-(1,2,4-triazol-1-yl)-1-pentene-3-ol | 0 |
| 1-(4-fluorophenyl)-4-methoxy-4-methyl-2-(1,2,4-triazol-1-yl)-1-pentene-3-ol | 0 |
| Control | 4 |

EXAMPLE 11

In a greenhouse, the plants listed in the following table, in a stage of pre-germination, are treated with the compound according to the present invention in the application amounts given.

For this purpose, the compound was applied uniformly over the earth as a suspension with 500 liter water per hectare. 3 weeks after the treatment, classification is performed according to the classification scheme 0–10, whereby:
0 = destruction of the plants
1–4 = complete up to very strong inhibition of the plants
5–7 = strong to average inhibition of the plants
8–9 = little inhibition of the plants
10 = normal growth of the plants.

It is evident from the following Table that in particular several weeds are completely inhibited in their development by the compound according to the present invention, so that they can be eliminated as opposition. This effect can be used for weed control.

| Compound according to the Invention 1-(4-chlorophenyl)-4-methoxy-4-methyl-2-(1,2,4-triazol-1-yl)-1-pentene-3-ol | 0.3 kg/ha | 1.0 kg/ha | 3.0 kg/ha |
|---|---|---|---|
| Stellaria m. | 3 | 0 | 0 |
| Abutilon h. | 4 | 3 | 2 |
| Matricaria ch. | 0 | 0 | 0 |
| Viola t. | 0 | 0 | 0 |
| Centaurea c. | 4 | 2 | 1 |
| Amaranthus r. | 6 | 4 | 2 |
| Galium a. | | | |
| Chrsanthemum s. | 5 | 1 | 1 |
| Ipomea p. | 7 | 5 | 4 |
| Polygonum f. | 3 | 2 | 1 |
| Avena f. | 6 | 5 | 4 |
| Alopecuras m. | 8 | 6 | 5 |
| Echinochloa c.g. | 9 | 8 | 4 |
| Setaria i. | 7 | 6 | 4 |
| Digitaria s. | 7 | 5 | 3 |
| Cyperus es. | 8 | 4 | 3 |
| Sorghum h. | 10 | 5 | 4 |
| Poa a. | 5 | 3 | 1 |
| Control | | 10 | |

EXAMPLE 12

Prophylactic Effectiveness of Leaf Treatment Against Erysiphe cichoracearum with Pumpkin Plants in a Greenhouse

Young pumpkin plants are sprayed dripping wet with the active substance concentrations set forth in the following table. After drying of the spray coating, they are inoculated by dusting with dry mildew spores of *Erysiphe cichoracearum*. In comparison, untreated plants are inoculated as control. The plants are incubated in a greenhouse at 24° C. After 1 week, the affected leaf surface is calculated as a percent of the total leaf surface. The fungicidal activity is determined as follows:

$$100 - \frac{100 \cdot \text{affect in treated}}{\text{affect in untreated}} = \% \text{ Effectiveness}$$

The compounds are provided as 20% formulations:

TABLE

| | % Effectiveness against *Erysiphe cichoracearum* | |
|---|---|---|
| Compound according to the Invention | Active Agent Concentration | |
| | 0.025% | 0.005% |
| 1-(4-chlorophenyl)-4-methoxy-4-methyl-2-(1,2,4-triazol-1-yl)-1-pentene-3-one | 100 | 100 |
| 10(2-chlorophenyl)-4-methoxy-4-methyl-2-(1,2,4-triazol-1-yl)-1-pentene-3-one | 100 | 100 |
| 1-(2,4-dichlorophenyl)-4-methoxy-4-methyl-2-(1,2,4-triazol-1-yl)-1-pentene-3-one | 100 | 60 |
| 1-(2,6-dichlorophenyl)-4-methoxy-4-methyl-2-(1,2,4-triazol-1-yl)-1-pentene-3-one | 100 | 95 |
| 4-methoxy-4-methyl-1-phenyl-2-(1,2,4-triazol-1-yl)-1-pentene-3-one | 100 | 95 |
| 1-(4-chlorophenyl)-2-(imidazol-1-yl)-4-methoxy-4-methyl-1-pentene-3-one | 100 | 100 |
| 4-methoxy-4-methyl-1-(2-thienyl)-2-(1,2,4-triazol-1-yl)-1-pentene-3-one | 100 | 94 |
| 2-(imidazol-1-yl)-4-methoxy-4-methyl-1-(2-thienyl)-1-pentene-3-one | 100 | 90 |
| 1-(2,4-dichlorophenyl)-2-(imidazol-1-yl)-4-methoxy-4-methyl-1-pentene-3-one | 100 | 100 |
| 1-(2,6-dichlorophenyl)-2-(imidazol-1-yl)-4-methoxy-4-methyl-1-pentene-3-one | 100 | 100 |
| 1-(2-chlorophenyl)-2-(imidazol-1-yl)-4-methoxy-4-methyl-1-pentene-3-one | 100 | 100 |
| 2-(imidazol-1-yl)-4-methoxy-4-methyl-1-phenyl-1-pentene-3-one | 100 | 98 |
| 1-(4-chlorophenyl)-4-methoxy-4-methyl-2-(1,2,4-triazol-1-yl)-1-pentene-3-ol | 100 | 100 |
| 1-(2,4-dichlorophenyl)-4-methoxy-4-methyl-2-(1,2,4-triazol-1-yl)-1-pentene-3-ol | 100 | 100 |
| 1-(3,4-dichlorophenyl)-4-methoxy-4-methyl-2-(1,2,4-triazol-1-yl)-1-pentene-3-one naphthalindisulfonate | 100 | |
| 1-(2-chlorophenyl)-4-methoxy-4-methyl-2-(1,2,4-triazol-1-yl)-1-pentene-3-ol | 100 | |
| 4-methoxy-4-methyl-1-(2-thienyl)-2-(1,2,4-triazol-1-yl)-1-pentene-3-one | 100 | |
| 1-(4-bromophenyl)-4-methoxy-4-methyl-2-(1,2,4-triazol-1-yl)-1-pentene-3-one | 100 | |

EXAMPLE 13

**Effectiveness of Leaf Treatment Against *Piricularia oryzae* with Rice Seedlings in a Greenhouse**

Young rice plants sprayed dripping wet with 0.1% active substance concentration. After drying of the spray coating, the treated plants as well as untreated plants are inoculated by spraying of a suspension of spores (about 200,000/ml) of the leaf spot inducing *Piricularia oryzae,* and incubated moist in a greenhouse at +25° to +27° C.

After 5 days the percent of leaf surface affected is determined. From these numbers the fungicidal effectiveness is calculated as follows:

$$100 - \frac{100 \cdot \text{Affect in treated plants}}{\text{Affect in untreated}} = \% \text{ Effectiveness}$$

The compounds are provided as 20% formulations:

TABLE

| % Effectiveness against *Piricularia oryzae* | |
|---|---|
| Compound according to the Invention | Active Agent Concentration 0.1% |
| 1-(4-chlorophenyl)-4-methoxy-4-methyl-2-(1,2,4-triazol-1-yl)-1-pentene-3-one | 82 |
| 1-(2-chlorophenyl)-4-methoxy-4-methyl-2-(1,2,4-triazol-1-yl)-1-pentene-3-one | 90 |
| 1-(4-chlorophenyl)-2-(imidazol-1-yl)-4-methoxy-4-methyl-1-pentene-3-one | 82 |
| 2-(imidazol-1-yl)-4-methoxy-4-methyl-1-(2-thienyl)-1-pentene-3-one | 80 |
| 1-(4-chlorophenyl)-4-methoxy-4-methyl-2-(1,2,4-triazol-1-yl)-1-pentene-3-ol | 80 |

EXAMPLE 14

Propylactic Effectiveness of Leaf Treatment against *Plasmopara viticola* with Grape-Vine Plants in a Greenhouse Young grape-vine plants with about 5-8 leaves are sprayed dripping wet with 0.025% effective substance concentration, and after drying of the spray coatings, the leaf undersides are sprayed with an aqueous deposit of Sporangia of the fungus (about 20,000 per ml), after which they are incubated in a greenhouse at 22° to 24° C. in an atmosphere as water vapor saturated as possible. From the second day on, the air moisture is returned to normal level for 3 to 4 days (30–70% saturation), and then for 1 day maintained at a level of water vapor saturation. Subsequently, for each leaf, the percent portion of fungus-affected surface is noted, and the average per treatment is used for determination of the fungicidal effectiveness as follows:

$$100 - \frac{100 \cdot \text{Affect in treated plants}}{\text{Affect in untreated}} = \% \text{ Effectiveness}$$

The compounds are provided as 20% formulations.

TABLE

| % Effectiveness against *Plasmopora viticola* | |
|---|---|
| Compound according to the Invention | Active Agent Concentration 0.025% |
| 1-(2-chlorophenyl)-4-methoxy-4-methyl-2-(1,2,4-triazol-1-yl)-1-pentene-3-one | 98 |
| 1-(2,4-dichlorophenyl)-4-methoxy-4-methyl-2-(1,2,4-triazol-1-yl)-1-pentene-3-one | 80 |
| 1-(2,4-dichlorophenyl)-2-(imidazol-1-yl)-4-methoxy-4-methyl-1-pentene-3-one | 80 |
| 1-(2,6-dichlorophenyl)-2-(imidazol-1-yl)-4-methoxy-4-methyl-1-pentene-3-one | 80 |

EXAMPLE 15

Propylactic Effectiveness of Leaf Treatment Against *Botrytis cinerea* with Tomato Seedlings in a Greenhouse Young tomato plants are treated dripping wet with spray liquid containing 0.025% active substance. After drying of the spray coatings, the treated plants as well as untreated plants, as control, are inocculated. For this, as inocculate, a suspension of spores (about 1 million per milliliter fruit juice solution) of the gray mold stimulating *Botrytis cinerea* is sprayed onto the plants. Subsequently the plants are incubated in a greenhouse at about 20° C. and with high air moisture. After the collapse of the untreated plants (=100% affect), the degree of affect for the treated plants is determined and the fungicidal effectiveness calculated as follows:

$$100 - \frac{100 \cdot \text{Affect in treated plants}}{\text{Affect in untreated}} = \% \text{ Effectiveness}$$

The compound according to the present invention 1-(2,4-dichlorophenyl)-2-(imidazol-1-yl)-4-methoxy-4-methyl-1-pentene-3-one, used in 20% formulation, limited the affect about 80%.

EXAMPLE 16

Seed Treatment against *Helminthosporium gramineum*

Barley seeds, naturally affected by *Helminthosporium gramineum,* either untreated or treated (see Table), are sowed with earth in a plant vessel, and allowed to germinate at temperatures below 16° C. After the germination, for 12 hours daily, the plants are illuminated. After about 5 weeks, the affected plants are counted and compared with the total amount of plants per test series. The fungicidal effectiveness is calculated as follows:

$$100 - \frac{100 \cdot \text{Affect in treated plants}}{\text{Affect in untreated}} = \% \text{ Effectiveness}$$

The compounds are provided as 20% formulations.

TABLE

| % Effectiveness against *Helminthosporium gramineum* | |
|---|---|
| Compound according to the Invention | 50 g active agent/ 100 kg |
| 1-(4-chlorophenyl)-4-methoxy-4-methyl-2-(1,2,4-triazol-1-yl)-1-pentene-3-one | 75 |
| 1-(2-chlorophenyl)-4-methoxy-4-methyl-2-(1,2,4-triazol-1-yl)-1-pentene-3-one | 70 |
| 1-(2,4-dichlorophenyl)-4-methoxy-4-methyl-2-(1,2,4-triazol-1-yl)-1-pentene-3-one | 60 |
| 4-methoxy-4-methyl-1-phenyl-2-(1,2,4-triazol-1-yl)-1-pentene-3-one | 90 |
| 1-(4-chlorophenyl)-2-(imidazol-1-yl)-4-methoxy-4-methyl-1-pentene-3-one | 60 |
| 2-(imidazol-1-yl)-4-methoxy-4-methyl-1-(2-thienyl)-1-pentene-3-one | 65 |
| 1-(2-chlorophenyl)-2-(imidazol-1-yl)-4-methoxy-4-methyl-1-pentene-3-one | 65 |
| 2-(imidazol-1-yl)-4-methoxy-4-methyl-1-phenyl-1-pentene-3-one | 60 |

EXAMPLE 17

Systematic effectiveness of Seed Treatment against Grain-Mildew *Erysiphe graminis* with Barley Seeds of the summer barley MGZ, either untreated or treated, are sowed with earth in a plant vessel, and allowed to germinate at temperatures of about 20° C. in a greenhouse. After the formation of the first true leaves, the plants are inoculated by coating with mildew-affected plants. One week later the percent of leaf surface covered by mildew is noted.

The fungicidal effectiveness is calculated as follows:

$$100 - \frac{100 \cdot \text{Affect in treated plants}}{\text{Affect in untreated}} = \% \text{ Effectiveness}$$

The compounds according to the present invention are provided as 20% formulations.

TABLE

| % Effectiveness against *Erysiphe graminis* | |
|---|---|
| Compound of the Invention | 50 g Active Agent/ 100 kg |
| 1-(4-chlorophenyl)-4-methoxy-4-methyl-2-1,2,4-triazol-1-yl)-1-pentene-3-one | 100 |
| 1-(2,4-dichlorophenyl)-4-methoxy-4-methyl-2-(1,2,4-triazol-1-yl)-1-pentene-3-one | 100 |
| 1-(4-chlorophenyl)-2-(imidazol-1-yl)-4-methoxy-4-methyl-1-pentene-3-one | 90 |
| 1-)4-chlorophenyl)-4-methoxy-4-methyl-2-(1,2,4-triazol-1-yl)-1-pentene-3-ol | 100 |

EXAMPLE 18

Effectiveness of Seed Treatment against *Tilletia caries* with Wheat

Wheat seeds are contaminated with 3 g spores of the smut-inducing *Tilletia caries* per kg. Untreated as well as treated grains are pressed with their bearded ends into Petrie dishes with moist loam, and incubated at temperatures below 12° C. for 3 days. Subsequently, the grains are removed and the Petrie dishes with the remaining smut spores are further incubated at temperatures below 12° C. After 10 days, the spores are examined for germination. The fungical effectiveness is calculated as follows:

$$100 - \frac{100 \cdot \text{Germ-\% in treated}}{\text{Germ-\% in untreated}} = \% \text{ Effectiveness}$$

The compounds are provided as 20% formulations.

TABLE

| % Effectiveness of the seed treatment against *Tilletia caries* | |
|---|---|
| Compound of the Invention | 50 g Active Agent/ 100 kg |
| 1-(4-chlorophenyl)-4-methoxy-4-methyl-2-(1,2,4-triazol-1-yl)-1-pentene-3-one | 100 |
| 1-(2-chlorophenyl)-4-methoxy-4-methyl-2-(1,2,4-triazol-1-yl)-1-pentene-3-one | 100 |
| 1-(2,4-dichlorophenyl)-4-methoxy-4-methyl-2-(1,2,4-triazol-1-yl)-1-pentene-3-one | 100 |
| 4-methoxy-4-methyl-1-phenyl-2-(1,2,4-triazol-1-yl)-1-pentene-3-one | 90 |

EXAMPLE 19

Seed Treatment Against *Fusarium nivale* (*Gerlachia nivalis*) with Rye

Rye seeds, naturally affected by *Fusarium nivale*, are treated and sowed in a plant vessel along with untreated seeds (control). The temperature of the vessel is adjusted to 6° C. After the germination of the plants, the lighting is introduced and almost 100% relative air moisture is provided. 3 weeks after the sowing, the percent affected is determined. From the mean values of five repetitions, the fungicidal effectiveness is calculated.

$$100 - \frac{100 \cdot \text{Affect in treated plants}}{\text{Affect in untreated}} = \% \text{ Effectiveness}$$

The compounds are provided as 20% formulations.

TABLE

| % Effectiveness against *Fusarium nivale* | |
|---|---|
| Compound according to the Invention | 50 g Active Agent/100 kg |
| 4-methoxy-4-methyl-1-phenyl-2-(1,2,4-triazol-1-yl)-1-pentene-3-one | 82 |
| 1-(2,4-dichlorophenyl)-2-(imidazol-1-yl)-4-methoxy-4-methyl-1-pentene-3-one | 100 |
| 1-(4-chlorophenyl)-4-methoxy-4-methyl-2-(1,2,4-triazol-1-yl)-1-pentene-3-ol | 80 |

EXAMPLE 20

Prophylactic Effectiveness of Leaf Treatment Against *Helminthosporium teres* with Barley Plants in a Greenhouse Young barley plants are sprayed dripping wet with 0.05% active substance concentration. After drying of the spray coatings, the treated as well as untreated plants are sprayed with a suspension of Conidia (about 50,000 per ml) of *Helminthosporium teres*, and incubated moist in a greenhouse at 20°-22° C. After 1 week the percent effect on the leaves is noted. From the observed values the fungicidal effectiveness is calculated as follows:

$$100 - \frac{100 \cdot \text{Affect in treated plants}}{\text{Affect in untreated}} = \% \text{ Effectiveness}$$

The compounds are provided as 20% formulations.

TABLE

| % Effectiveness of the Prophylactive Spray Treatment | |
|---|---|
| Compounds according to the Invention | *Helminthosporium teres* 0.5% active agent |
| 2-(imidazol-1-yl)-4-methoxy-4-methyl-1-(2-thienyl)-1-pentene-3-one | 95 |
| 1-(2,6-dichlorophenyl)-2-(imidazol-1-yl)-4-methoxy-4-methyl-1-pentene-3-one | 90 |
| 1-(4-chlorophenyl)-4-methoxy-4-methyl-2-(1,2,4-triazol-1-yl)-1-pentene-3-ol | 95 |
| 1-(3,4-dichlorophenyl)-4-methoxy-4-methyl-1-(1,2,4-triazol-1-yl)-1-pentene-3-one naphthalindisulfonate | 89 |
| 1-(2-chlorophenyl)-4-methoxy-4-methyl-2-(1,2,4-triazol-1-yl)-1-pentene-3-ol | 94 |
| 1-(4-fluorophenyl)-4-methoxy-4-methyl-2-(1,2,4-triazol-1-yl)-1-pentene-3-one | 86 |
| 1-(3-chlorophenyl)-4-methoxy-4-methyl-2-(1,2,4-triazol-1-yl)-1-pentene-3-one | 95 |
| 1-(4-bromophenyl)-4-methoxy-4- | 95 |

TABLE-continued

% Effectiveness of the Prophylactive Spray Treatment

| Compounds according to the Invention | Helminthosporium teres 0.5% active agent |
|---|---|
| methyl-2-(1,2,4-triazol-1-yl)-1-pentene-3-ol | |
| 4-ethoxy-4-methyl-1-phenyl-2-(1,2,4-triazol-1-yl)-1-pentene-3-one | 95 |
| 4-ethoxy-1-(4-chlorophenyl)-4-methyl-2-(1,2,4-triazol-1-yl)-1-pentene-3-ol | 97 |

EXAMPLE 21

Prophylactive Effectiveness of Leaf Treatment Against *Erysiphe graminis* with Barley Plants in a Greenhouse Young barley plants are sprayed dripping wet with 0.05% active substance concentration. After drying of the spray coatings, the treated, as well as untreated plants, are inoculated, by rubbing affected plants across the test plants, so that the condiospores of *Erysiphe graminis* are transferred dry. Thereafter, the test plants are incubated in a greenhouse at 20°–22° C. After 1 week the percent affect of the leaves is noted. From the values, the fungicidal effectiveness is calculated as follows:

$$100 - \frac{100 \cdot \text{Affect in treated plants}}{\text{Affect in untreated}} = \% \text{ Effectiveness}$$

The compounds are provided as 20% formulations.

TABLE

% Effectiveness of the Prophylactic Spray Treatment

| Compound according to the Invention | Erysiphe graminis 0.05% Active Substance |
|---|---|
| 1-(3,4-dichlorophenyl)-4-methoxy-4-methyl-2-(1,2,4-triazol-1-yl)-1-pentene-3-one naphthalindisulfonate | 100 |
| 1-(2-chlorophenyl)-4-methoxy-4-methyl-2-(1,2,4-triazol-1-yl)-1-pentene-3-ol | 100 |
| 4-methoxy-4-methyl-1-(2-thienyl)-2-(1,2,4-triazol-1-yl)-1-pentene-3-ol | 90 |
| 4-ethoxy-(4-fluorophenyl)-4-methyl-2-(1,2,4-triazol-1-yl)-1-pentene-3-one | 90 |
| 1-(4-fluorophenyl)-4-methoxy-4-methyl-2-(1,2,4-triazol-1-yl)-1-pentene-3-one | 99 |
| 1-(3-chlorophenyl)-4-methoxy-4-methyl-2-(1,2,4-triazol-1-yl)-1-pentene-3-one | 100 |
| 1-(4-bromophenyl)-4-methoxy-4-methyl-2-(1,2,4-triazol-1-yl)-1-pentene-3-ol | 100 |
| 4-ethoxy-4-methyl-1-phenyl-2-(1,2,4-triazol-1-yl)-1-pentene-3-one | 98 |
| 4-ethoxy-4-methyl-1-(4-nitrophenyl)-2-(1,2,4,-triazol-1-yl)-1-pentene-3-one | 95 |
| 4-ethoxy-(3-chlorophenyl)-4-methyl-2-(1,2,4-triazol-1-yl)-1-pentene-3-one | 90 |
| 4-ethoxy-1-(4-chlorophenyl)-4-methyl-2-(1,2,4-triazol-1-yl)-1-pentene-3-ol | 99 |

EXAMPLE 22

Prophylactive Effectiveness of Leaf Treatment Against *Puccinia hordei* (midget rust) with Barley Plants in a Greenhouse Young barley plants are sprayed dripping wet with 0.05% active substance concentration. After drying of the spray coating, the treated, as well as untreated plants, are inoculated dry, by rubbing midget rust-affected plants across the test plants. Subsequently the test plants are incubated at 15°–17° C. in a greenhouse with high air moisture.

After another half week, the percent portion of affected leaf surfaces was noted. The fungicidal effectiveness is calculated as follows:

$$100 - \frac{100 \cdot \text{Affect in treated plants}}{\text{Affect in untreated}} = \% \text{ Effectiveness}$$

The compounds are provided as 20% formulations.

TABLE

% Effectiveness of Prophylactic Spray Treatment

| Compound according to the Invention | Puccinia hordei 0.05% Active Agent |
|---|---|
| 1-(4-chlorophenyl)-4-methoxy-4-methyl-2-(1,2,4-triazol-1-yl)-1-pentene-3-one | 100 |
| 1-(2-chlorophenyl)-4-methoxy-4-methyl-2-(1,2,4-triazol-1-yl)-1-pentene-3-one | 96 |
| 1-(2,4-dichlorophenyl)-4-methoxy-4-methyl-2-(1,2,4-triazol-1-yl)-1-pentene-3-one | 90 |
| 1-(2,6-dichlorophenyl)-4-methoxy-4-methyl-2-(1,2,4-triazol-1-yl)-1-pentene-3-one | 100 |
| 4-methoxy-4-methyl-1-phenyl-2-(1,2,4-triazol-1-yl)-1-pentene-3-one | 100 |
| 1-(4-chlorophenyl)-2-(imidazol-1-yl)-4-methoxy-4-methyl-1-pentene-3-one | 100 |
| 4-methoxy-4-methyl-1-(2-thienyl)-2-(1,2,4-triazol-1-yl)-1-pentene-3-one | 95 |
| 1-(2,4-dichlorophenyl)-2-(imidazol-1-yl)-4-methoxy-4-methyl-1-pentene-3-one | 100 |
| 1-(2,6-dichlorophenyl)-2-(imidazol-1-yl)-4-methoxy-4-methyl-1-pentene-3-one | 100 |
| 1-(2-chlorophenyl)-2-(imidazol-1-yl)-4-methoxy-4-methyl-1-pentene-3-one | 90 |
| 2-(imidazol-1-yl)-4-methoxy-4-methyl-1-phenyl-1-pentene-3-one | 100 |
| 1-(4-chlorophenyl)-4-methoxy-4-methyl-2-(1,2,4-triazol-1-yl)-1-pentene-3-ol | 100 |
| 1-(3,4-dichlorophenyl)-4-methoxy-4-methyl-2-(1,2,4-triazol-1-yl)-1-pentene-3-one, naphthalindisulfonate | 85 |
| 4-methoxy-4-methyl-1-(2-thienyl)-2-(1,2,4-triazol-1-yl)-1-pentene-3-ol | 90 |
| 1-(4-fluorophenyl)-4-methoxy-4-methyl-2-(1,2,4-triazol-1-yl)-1-pentene-3-one | 80 |
| 4-ethoxy-1-(4-chlorophenyl)-4-methyl-2-(1,2,4-triazol-1-yl)-1-pentene-3-ol | 85 |

It will be understood that each of the elements described above, or two or more together, may also find a useful application in other types of compounds differing from the types described above.

While the invention has been illustrated and described as embodied azolyl-pentene derivatives, methods for the production of these compounds, as well as biocidal compositions containing them, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Azolyl-pentene derivative of the formula

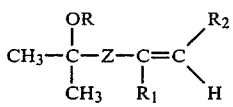

I in which

R is $C_1$–$C_{10}$-alkyl or $C_3$–$C_8$-alkenyl, $R_1$ is imidazol-1-yl or 1,2,4-triazol-1-yl, $R_2$ is phenyl, 2-fluorophenyl, 4-fluorophenyl, 2-chlorophenyl, 3-chlorophenyl, 4-chlorophenyl, 4-bromophenyl, 2,4-dichlorophenyl, 3,4-dichlorophenyl, 2,6-dichlorophenyl, 2-methylphenyl, 4-methylphenyl, 4-methoxyphenyl, 4-nitrophenyl, 2-naphthyl, 2-pyridyl, 3-pyridyl, 2-thienyl or 2-furyl, and Z is

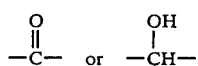

and its acid addition salt with an inorganic or an organic acid.

2. Azolyl-pentene derivative according to claim 1, wherein said acids are selected from the group consisting of hydrochloric acid, hydrobromic acid, phosphoric acid, sulfuric acid, nitric acid, acetic acid, maleic acid, oxalic acid, succinic acid, fumaric acid, tartaric acid, citric acid, salicylic acid, lactic acid, p-toluenesulfonic acid and 1,5-naphthalenedisulfionic acid.

3. The compound according to claim 1, which is 1-(4-chlorophenyl)-4-methoxy-2-(1,2,4-triazol-1-yl)-1-pentene-3-one.

4. The compound according to claim 1, which is 1-(4-chlorophenyl)-4-methoxy-4-methyl-2-(1,2,4-triazol-1-yl)-1-pentene-3-ol.

5. The compound according to claim 1, which is 1-(2-chlorophenyl)-4-methoxy-4-methyl-2-(1,2,4-triazol-1-yl)-1-pentene-3-one.

6. The compound according to claim 1, which is 1-(2,4-dichlorophenyl)-4-methoxy-4-methyl-2-(1,2,4-triazol-1-yl)-1-pentene-3-one.

7. The compound according to claim 1, which is 1-(2,6-dichlorophenyl)-4-methoxy-4-methyl-2-(1,2,4-triazol-1-yl)-1-pentene-3-one.

8. The compound according to claim 1, which is 4-methoxy-4-methyl-1-phenyl-2-(1,2,4-triazol-1-yl)-1-pentene-3-one.

9. The compound according to claim 1, which is 1-(4-chlorophenyl)-2-(imidazol-1-yl)-4-methoxy-4-methyl-1-pentene-3-one.

10. The compound according to claim 1, which is 4-methoxy-4-methyl-1-(2-thienyl)-2-(1,2,4-triazol-1-yl)-1-pentene-3-one.

11. The compound according to claim 1, which is 2-(imidazol-1-yl)-4-methoxy-4-methyl-1-(2-thienyl)-1-pentene-3-one.

12. The compound according to claim 1, which is 1-(2,4-dichlorophenyl)-2-(imidazol-1-yl)-4-methoxy-4-methyl-1-pentene-3-one.

13. The compound according to claim 1, which is 1-(2,6-dichlorophenyl)-2-(imidazol-1-yl)-4-methoxy-methyl-1-pentene-3-one.

14. The compound according to claim 1, which is 1-(2-chlorophenyl)-2-(imidazol-1-yl)-4-methyl-1-pentene-3-one.

15. The compound according to claim 1, which is 2-(imidazol-1-yl)-4-methoxy-4-methyl-1-phenyl-1-pentene-3-one.

16. The compound according to claim 1, which is 1-(2,4-dichlorophenyl)-4-methoxy-4-methyl-2-(1,2,4-triazol-1-yl)-1-pentene-3-ol.

17. The compound according to claim 1, which is 1-(3,4-dichlorophenyl)-4-methoxy-4-methyl-2-(1,2,4-triazol-1-yl)-1-pentene-3-one, naphthalenedisulfonate.

18. The compound according to claim 1, which is 1-(2,6-dichlorophenyl)-4-methoxy-4-methyl-2-(1,2,4-triazol-1-yl)-1-pentene-3-ol.

19. The compound according to claim 1, which is 1-(2-chlorophenyl)-4-methoxy-4-methyl-2-(1,2,4-triazol-1-yl)-1-pentene-3-ol.

20. The compound according to claim 1, which is 4-methoxy-4-methyl-1-(2-thienyl)-2-(1,2,4-triazol-1-yl)-1-pentene-3-ol.

21. The compound according to claim 1, which is 1-(4-bromophenyl)-4-methoxy-4-methyl-2-(1,2,4-triazol-1-yl)-1-pentene-3-one.

22. The compound according to claim 1, which is 4-ethoxy-1-(4-chlorophenyl)-4-methyl-2-(1,2,4-triazol-1-yl)-1-pentene-3-one.

23. The compound according to claim 1, which is 4-ethoxy-1-(4-fluorophenyl)-4-methyl-2-(1,2,4-triazol-1-yl)-1-pentene-3-one.

24. The compound according to claim 1, which is 1-(4-fluorophenyl)-4-methoxy-4-methyl-2-(1,2,4-triazol-1-yl)-1-pentene-3-one.

25. The compound according to claim 1, which is 1-(3-chlorophenyl)-4-methoxy-4-methyl-2-(1,2,4-triazol-1-yl)-1-pentene-3-one.

26. The compound according to claim 1, which is 1-(4-bromophenyl)-4-methoxy-4-methyl-2-(1,2,4-triazol-1-yl)-1-pentene-3-ol.

27. The compound according to claim 1, which is 4-ethoxy-4-methyl-1-phenyl-2-(1,2,4-triazol-1-yl)-1-pentene-3-one.

28. The compound according to claim 1, which is 4-ethoxy-1-(2-chlorophenyl)-4-methyl-2-(1,2,4-triazol-1-yl)-1-pentene-3-one.

29. The compound according to claim 1, which is 4-ethoxy-4-methyl-1-(4-nitrophenyl)-2-(1,2,4-triazol-1-yl)-1-pentene-3-one.

30. The compound according to claim 1, which is 4-ethoxy-(3-chlorophenyl)-4-methyl-2-(1,2,4-triazol-1-yl)-1-pentene-3-one.

31. The compound according to claim 1, which is 4-ethoxy-1-(4-chlorophenyl)-4-methyl-2-(1,2,4-triazol-1-yl)-1-pentene-3-ol.

32. The compound according to claim 1, which is 1-(4-fluorophenyl)-4-methoxy-4-methyl-2-(1,2,4-triazol-1-yl)-1-pentene-3-ol.

33. The compound according to claim 1, which is 4-ethoxy-1-(4-bromophenyl)-4-methyl-2-(1,2,4-triazol-1-yl)-1-pentene-3-one.

34. The compound according to claim 1, which is 4-ethoxy-1-(2,4-dichlorophenyl)-4-methyl-2-(1,2,4-triazol-1-yl)-1-pentene-3-one.

35. The compound according to claim 1, which is 4-ethoxy-1-(3,4-dichlorophenyl)-4-methyl-2-(1,2,4-triazol-1-yl)-1-pentene-3-one.

36. The compound according to claim 1, which is 4-ethoxy-4-methyl-1-(4-methylphenyl)-2-(1,2,4-triazol-1-yl)-1-pentene-3-one.

37. The compound according to claim 1, which is 4-ethoxy-4-methyl-1-phenyl-2-(1,2,4-triazol-1-yl)-1-pentene-3-ol.

38. The compound according to claim 1, which is 4-ethoxy-1-(4-fluorophenyl)-4-methyl-2-(1,2,4-triazol-1-yl)-1-pentene-3-ol.

39. The compound according to claim 1, which is 4-ethoxy-1-(2-chlorophenyl)-4-methyl-2-(1,2,4-triazol-1-yl)-1-pentene-3-ol.

40. The compound according to claim 1, which is 1-(2-fluorophenyl)-4-methoxy-4-methyl-2-(1,2,4-triazol-1-yl)-1-pentene-3-one.

41. The compound according to claim 1, which is 4-methoxy-1-(4-methoxyphenyl)-4-methyl-2-(1,2,4-triazol-1-yl)-1-pentene-3-one.

42. The compound according to claim 1, which is 4-ethoxy-4-methyl-1-(4-nitrophenyl)-2-(1,2,4-triazol-1-yl)-1-pentene-3-ol.

43. The compound according to claim 1, which is 4-ethoxy-1-(4-bromophenyl)-4-methyl-2-(1,2,4-triazol-1-yl)-1-pentene-3-ol.

44. The compound according to claim 1, which is 4-ethoxy-1-(2,4-dichlorophenyl)-4-methyl-2-(1,2,4-triazol-1-yl)-1-pentene-3-ol.

45. The compound according to claim 1, which is 4-ethoxy-1-(3,4-dichlorophenyl)-4-methyl-2-(1,2,4-triazol-1-yl)-1-pentene-3-ol.

46. The compound according to claim 1, which is 4-ethoxy-4-methyl-1-(4-methylphenyl)-2-(1,2,4-triazol-1-yl)-1-pentene-3-ol.

47. The compound according to claim 1, which is 4-ethoxy-1-(4-methoxyphenyl)-4-methyl-2-(1,2,4-triazol-1-yl)-1-pentene-3-one.

48. The compound according to claim 1, which is 4-ethoxy-1-(2-furyl)-4-methyl-2-(1,2,4-triazol-1-yl)-1-pentene-3-one.

49. The compound according to claim 1, which is 4-ethoxy-1-(2-furyl)-4-methyl-2-(1,2,4-triazol-1-yl)-1-pentene-3-ol.

50. The compound according to claim 1, which is 4-ethoxy-4-methyl-1-(2-thienyl)-2-(1,2,4-triazol-1-yl)-1-pentene-3-ol.

51. The compound according to claim 1, which is 4-ethoxy-4-methyl-1-(3-pyridyl)-2-(1,2,4-triazol-1-yl)-1-pentene-3-one.

52. The compound according to claim 1, which is 4-ethoxy-4-methyl-1-(3-pyridyl)-2-(1,2,4-triazol-1-yl)-1-pentene-3-ol.

53. The compound according to claim 1, which is 4-ethoxy-4-methyl-1-(2-naphthyl)-2-(1,2,4-triazol-1-yl)-1-pentene-3-one.

54. The compound according to claim 1, which is 4-ethoxy-4-methyl-1-(2-naphthyl)-2-(1,2,4-triazol-1-yl)-1-pentene-3-ol.

55. The compound according to claim 1, which is 4-methoxy-4-methyl-1-(4-methylphenyl)-2-(1,2,4-triazol-1-yl)-1-pentene-3-one.

56. The compound according to claim 1, which is 4-methoxy-4-methyl-1-(4-methylphenyl)-2-(1,2,4-triazol-1-yl)-1-pentene-3-ol.

57. The compound according to claim 1, which is 4-methoxy-1-(4-methoxyphenyl)-4-methyl-2-(1,2,4-triazol-1-yl)-1-pentene-3-ol.

58. The compound according to claim 1, which is 4-methoxy-4-methyl-1-phenyl-2-(1,2,4-triazol-1-yl)-1-pentene-3-ol.

59. The compound according to claim 1, which is 1-(3,4-dichlorophenyl)-4-methoxy-4-methyl-2-(1,2,4-triazol-1-yl)-1-pentene-3-one.

60. The compound according to claim 1, which is 1-(3,4-dichlorophenyl)-4-methoxy-4-methyl-2-(1,2,4-triazol-1-yl)-1-pentene-3-ol.

61. The compound according to claim 1, which is 4-methoxy-4-methyl-1-(4-nitrophenyl)-2-(1,2,4-triazol-1-yl)-1-pentene-3-one.

62. The compound according to claim 1, which is 4-methoxy-4-methyl-1-(4-nitrophenyl)-2-(1,2,4-triazol-1-yl)-1-pentene-3-ol.

63. The compound according to claim 1, which is 4-methoxy-4-methyl-1-(2-methylphenyl)-2-(1,2,4-triazol-1-yl)-1-pentene-3-one.

64. The compound according to claim 1, which is 4-methoxy-4-methyl-1-(2-methylphenyl)-2-(1,2,4-triazol-1-yl)-1-pentene-3-ol.

65. The compound according to claim 1, which is 1-(2-chlorophenyl)-2-(imidazol-1-yl)-4-methoxy-4-methyl-1-pentene-3-ol.

66. The compound according to claim 1, which is 1-(4-chlorophenyl)-2-(imidazol-1-yl)-4-methoxy-4-methyl-1-pentene-3-ol.

67. The compound according to claim 1, which is 4-ethoxy-1-(2-fluorophenyl)-4-methyl-2-(1,2,4-triazol-1-yl)-1-pentene-3-ol.

68. The compound according to claim 1, which is 1-(3-chlorophenyl)-4-methoxy-4-methyl-2-(1,2,4-triazol-1-yl)-1-pentene-3-ol.

69. The compound according to claim 1, which is 4-ethoxy-4-methyl-1-(2-methylphenyl)-2-(1,2,4-triazol-1-yl)-1-pentene-3-one.

70. The compound according to claim 1, which is 4-ethoxy-4-methyl-1-(2-thienyl)-2-(1,2,4-triazol-1-yl)-1-pentene-3-one.

71. The compound according to claim 1, which is 4-n-butoxy-1-(4-chlorophenyl)-4-methyl-2-(1,2,4-triazol-1-yl)-1-pentene-3-ol.

72. The compound according to claim 1, which is 4-n-butoxy-1-(2-chlorophenyl)-4-methyl-2-(1,2,4-triazol-1-yl)-1-pentene-3-ol.

73. The compound according to claim 1, which is 4-ethoxy-1-(2-fluorophenyl)-4-methyl-2-(1,2,4-triazol-1-yl)-1-pentene-3-one.

74. The compound according to claim 1, which is 4-(n-butoxy)-1-(4-chlorophenyl)-4-methyl-2-(1,2,4-triazol-1-yl)-1-pentene-3-one.

75. The compound according to claim 1, which is 4-(n-butoxy)-1-(2-chlorophenyl)-4-methyl-2-(1,2,4-triazol-1-yl)-1-pentene-3-one.

76. The compound according to claim 1, which is 4-methoxy-4-methyl-1-(2-pyridyl)-2-(1,2,4-triazol-1-yl)-1-pentene-3-ol.

77. The compound according to claim 1, which is 4-ethoxy-4-methyl-1-(2-methylphenyl)-2-(1,2,4-triazol-1-yl)-1-pentene-3-ol.

* * * * *

Notice of Adverse Decisions in Interference

In Interference No. 102,241, involving Patent No. 4,517,367, C. Skotsch, D. Baumert, H. Krahmer and F. Arndt, AZOLYL-PENTENE DERIVATIVES AND BIOCIDAL COMPOSITIONS CONTAINING THE SAME, final judgment adverse to the patentees was rendered November 28, 1989, as to claims 1-77.

*(Official Gazette February 20, 1990)*